US011583179B2

United States Patent
Qian et al.

(10) Patent No.: US 11,583,179 B2
(45) Date of Patent: Feb. 21, 2023

(54) LENS FITTING METROLOGY WITH OPTICAL COHERENCE TOMOGRAPHY

(71) Applicant: Meta Platforms Technologies, LLC, Menlo Park, CA (US)

(72) Inventors: Ruobing Qian, Redmond, WA (US); Mohamed Tarek El-Haddad, Redmond, WA (US); Robin Sharma, Redmond, WA (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 195 days.

(21) Appl. No.: 16/920,228

(22) Filed: Jul. 2, 2020

(65) Prior Publication Data

US 2021/0259541 A1    Aug. 26, 2021

Related U.S. Application Data

(60) Provisional application No. 62/979,337, filed on Feb. 20, 2020.

(51) Int. Cl.
*G01B 9/02* (2022.01)
*A61B 3/10* (2006.01)
(Continued)

(52) U.S. Cl.
CPC .......... *A61B 3/102* (2013.01); *G01B 9/02091* (2013.01); *G01S 17/894* (2020.01)

(58) Field of Classification Search
CPC ..... A61B 3/102; A61B 5/0066; A61B 5/0073; G01S 17/894; G01B 9/02091; G01B 9/02029; G01B 9/0203
See application file for complete search history.

(56) References Cited

U.S. PATENT DOCUMENTS

2008/0204655 A1 *  8/2008  Kikawa .............. G01B 9/02089
                                                           351/206
2009/0268209 A1 * 10/2009  Waelti ................ G01B 9/02091
                                                           356/479
(Continued)

FOREIGN PATENT DOCUMENTS

JP          2018201858 A        12/2018

OTHER PUBLICATIONS

Xiaojing Liu, Chia-Hao Wang, Cuixia Dai, Adam Camesa, Hao F. Zhang & Shuliang Jiao (2013) Effect of Contact Lens on Optical Coherence Tomography Imaging of Rodent Retina, Current Eye Research, 38:12, 1235-1240, DOI: 10.3109/02713683.2013.815218 (Year: 2013).*

(Continued)

*Primary Examiner* — Tarifur R Chowdhury
*Assistant Examiner* — Jonathon Cook
(74) *Attorney, Agent, or Firm* — Freestone Intellectual Property Law PLLC; Aaron J. Visbeek

(57) ABSTRACT

Sensor data is captured with a sensor. The sensor data includes a lens-position of a prescription lens relative to a reference point of an optical coherence tomography (OCT) system. A mirror of a reference arm of the OCT system is positioned at an optical pathlength between an eye region of the prescription lens based at least in part on the sensor data. An OCT signal is generated while the mirror is positioned at the optical pathlength. At least one depth profile is generated that includes the prescription lens and the eye region.

20 Claims, 14 Drawing Sheets

(51) Int. Cl.
  *G01S 17/894* (2020.01)
  *G01B 9/02091* (2022.01)

(56) References Cited

U.S. PATENT DOCUMENTS

| | | | |
|---|---|---|---|
| 2010/0149489 A1* | 6/2010 | Kikawa | A61B 3/102 |
| | | | 351/206 |
| 2018/0116503 A1* | 5/2018 | Hogan | G02B 27/0068 |
| 2020/0100673 A1* | 4/2020 | Shimizu | A61B 3/14 |

OTHER PUBLICATIONS

Song, Shaozhen, Long-range and wide field of view optical coherence tomography . . . , Nov. 1, 2016,15, Biomedical Optics Express 4734,vol. 7.,No. 11.

Kalkman, J., Fourier-Domain Optical Coherence Tomography . . . , Mar. 22, 2017,17, Hindawi, International Journal of Optics,vol. 2017, ID 9586067.

Wikipedia, Optical coherence tomography, website, 19, Feb. 5, 2020 at 7:15 (UTC).

OCT Medical Imaging Optical Coherence Tomography Medical Imaging (Report Sample), Feb. 2018, 28, KnowMade, Ref.: KM18001.

Yaqoob, Zahid, Spectral domain optical coherence tomography . . . , Dec. 2005, 8, Molecular Imaging, Bio Techniques 39:S6-S13.

Bisch, Niklas, Why is Frequency Domain OCT named this way?, Feb. 2017, 7, https://www.researchgate.net/post/Why_is_Frequency . . . .

International Searching Authority, Patent Cooperation Treaty, European Application No. PCT/US2021/012855, dated May 7, 2021, 11 pages.

International Preliminary Report on Patentability for International Application No. PCT/US2021/012855, dated Sep. 1, 2022, 9 pages.

* cited by examiner

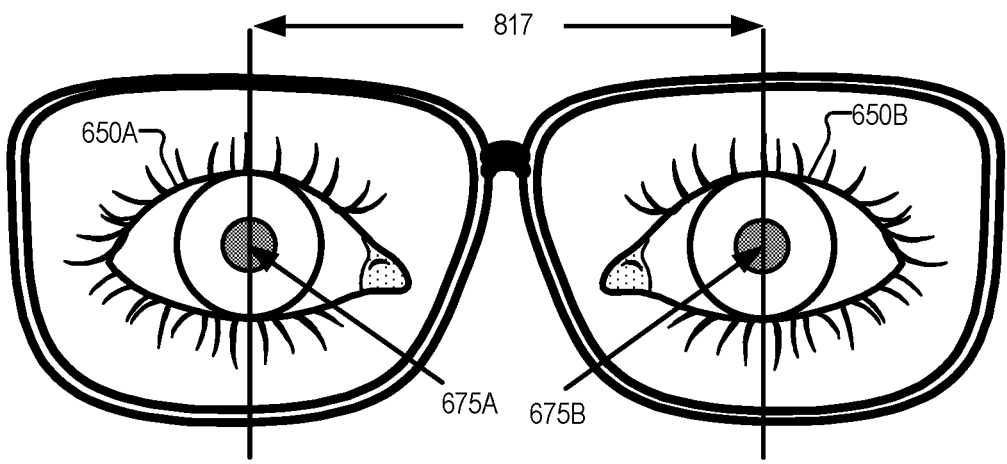
FIG. 8A
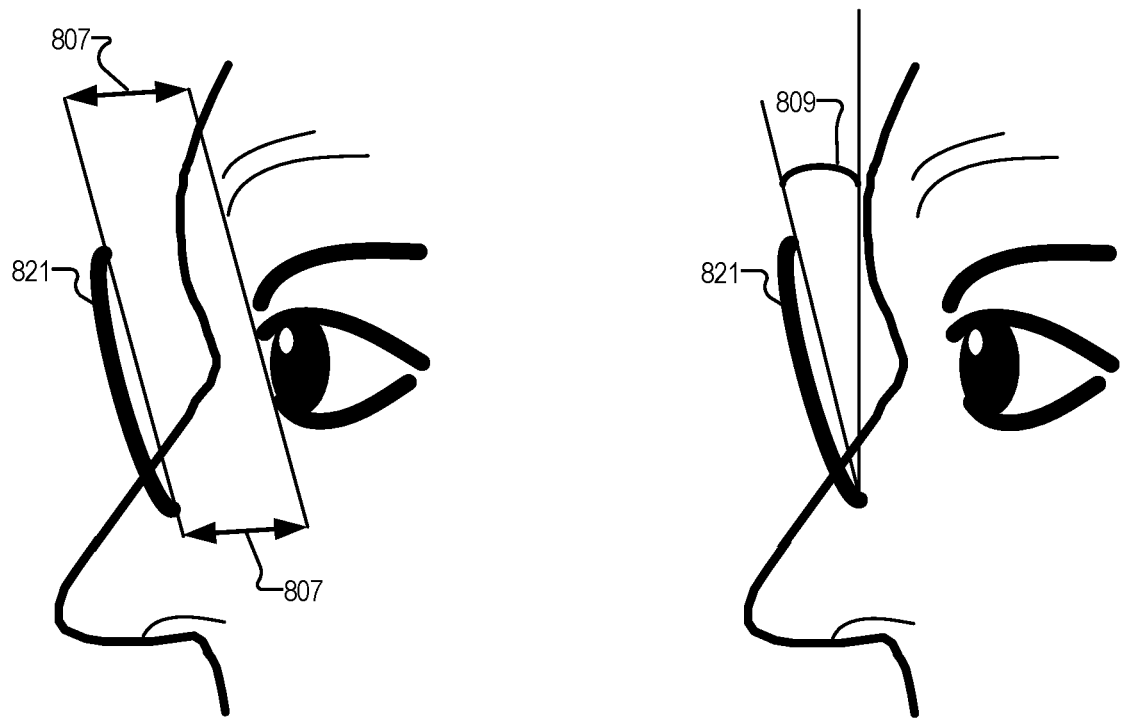
FIG. 8B
FIG. 8C

LENS FITTING METROLOGY WITH OPTICAL COHERENCE TOMOGRAPHY

CROSS REFERENCE TO RELATED APPLICATION

This application is a non-provisional application that claims priority under 35 U.S.C. § 119(e) to U.S. Provisional Application No. 62/979,337 filed Feb. 20, 2020, which is hereby incorporated by reference.

BACKGROUND INFORMATION

Obtaining prescription eyeglasses typically includes taking an eyeglass prescription to an optician or other optical professional and selecting eye-glass frames to hold the corrective lenses. However, the unique fit of prescription lenses and eye-glass frames relative to a face and positioning to the eye is highly variable. In this and other contexts, imaging prescription lenses with respect to the eye and/or face is useful.

BRIEF DESCRIPTION OF THE DRAWINGS

Non-limiting and non-exhaustive embodiments of the invention are described with reference to the following figures, wherein like reference numerals refer to like parts throughout the various views unless otherwise specified.

FIGS. 8A-8C illustrate various measurements from a volumetric ocular depth image, in accordance with aspects of the disclosure.

DETAILED DESCRIPTION

Figure 1:
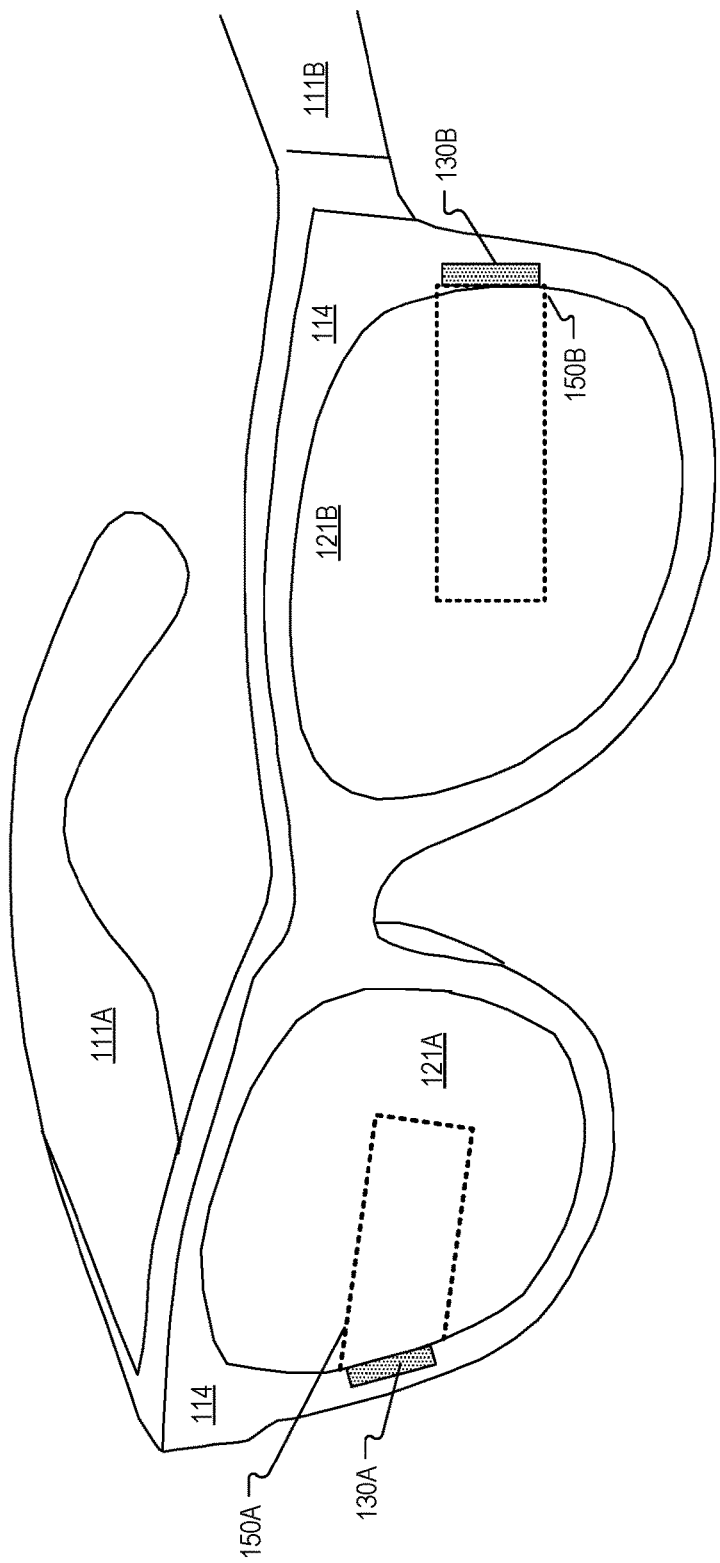
FIG. 1 illustrates an example head mounted device that may include corrective lenses that are fabricated based on a volumetric ocular depth image of a user wearing eyeglasses with corrective lenses, in accordance with aspects of the disclosure.

Embodiments for lens fitting metrology with optical coherence tomography (OCT) are described herein. In the following description, numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Embodiments of the disclosure are directed to lens fitting metrology with optical coherence tomography. In an example implementation, a sensor in a system captures sensor data of a lens-position of a prescription lens. A mirror of a reference arm of the OCT system is positioned according to the sensor data. One or more OCT signals are generated with the OCT system while the mirror of the reference arm is positioned at the optical pathlength. The optical pathlength may be between an eye region of user's eye and a prescription lens worn by the user. One or more depth profiles is generated from the OCT signal(s) and the depth profiles may be used to generate a volumetric ocular depth image. The volumetric ocular depth image may include a variety of measurements of an eye region with respect to the prescription lens(es). For example, the volumetric ocular depth image may include an eye-relief distance with respect to the prescription lens, a lens-to-cornea distance, an interpupillary distance of the eye with respect to a second eye of the user, a pupil size of the eye, and/or a corneal topography of the eye. These measurements of the eye region with the respect to the prescription lenses worn by a person may allow for additional prescription lenses to be fitted to a specific user in a more particular manner.

The techniques, devices, and systems described in this disclosure may be used to assist in generating prescription lenses or other components for a head mounted device, head mounted displays, helmet mounted optical systems, and other optical systems that are to be worn on or about the head of a user. The techniques, devices, and systems described herein may also be used to measure various optical components of devices with respect to a face of a user. Furthermore, the devices and systems described in this disclosure may extract and export surface curvatures of contact lenses as well as corneal and ocular surface profiles. These and other embodiments are described in more detail in connection with FIGS. 1-11.

FIG. 1 illustrates an example head mounted device 100 that may include corrective lenses 121 that are fabricated based on a volumetric ocular depth image of a user wearing eyeglasses with corrective lenses, in accordance with aspects of the disclosure. Head mounted device 100 may be considered an AR or mixed reality (MR) head mounted display, in some aspects of the disclosure. In some aspects, head mounted device 100 does not necessarily include a display but does include electronics of some kind such as one or more cameras, speakers, eye-tracking sensor modules, other sensors, processors, and/or memory.

In FIG. 1, example head mounted device 100 includes frame 114 coupled to arms 111A and 111B. Lenses 121A and 121B are mounted to frame 114. Lenses 121 may include optical power matched to a particular wearer of head mounted device 100. The illustrated head mounted device 100 is configured to be worn on or about a head of a user.

Each lens 121 may optionally include a waveguide 150 to direct image light generated by a display 130 to an eyebox area for viewing by a wearer of head mounted device 100. Display 130 may include an LCD, an organic light emitting diode (OLED) display, micro-LED display, quantum dot display, pico-projector, or liquid crystal on silicon (LCOS) display for directing image light to a wearer of head mounted device 100.

The frame 114 and arms 111 of the head mounted device 100 may include supporting hardware of head mounted device 100. Head mounted device 100 may include any of processing logic, wired and/or wireless data interface for sending and receiving data, graphic processors, and one or more memories for storing data and computer-executable instructions. In one embodiment, head mounted device 100 may be configured to receive wired power. In one embodiment, head mounted device 100 is configured to be powered by one or more batteries. In one embodiment, head mounted device 100 may be configured to receive wired data including video data via a wired communication channel. In one embodiment, head mounted device 100 is configured to receive wireless data including video data via a wireless communication channel.

Lenses 121 may appear transparent to a user to facilitate augmented reality or mixed reality where a user can view scene light from the environment around her while also receiving image light directed to her eye(s) by waveguide(s) 150. Consequently, lenses 121 may be considered (or include) an optical combiner. In some embodiments, image light is only directed into one eye of the wearer of head mounted device 100. In an embodiment, both displays 130A and 130B are included to direct image light into waveguides 150A and 150B, respectively. Lenses 121 may include prescription optical elements that are specific to a user and thus designing the prescription optical elements may benefit from a volumetric ocular depth image that includes prescription lens(es) with respect to a user's eye and/or face.

Figure 2:
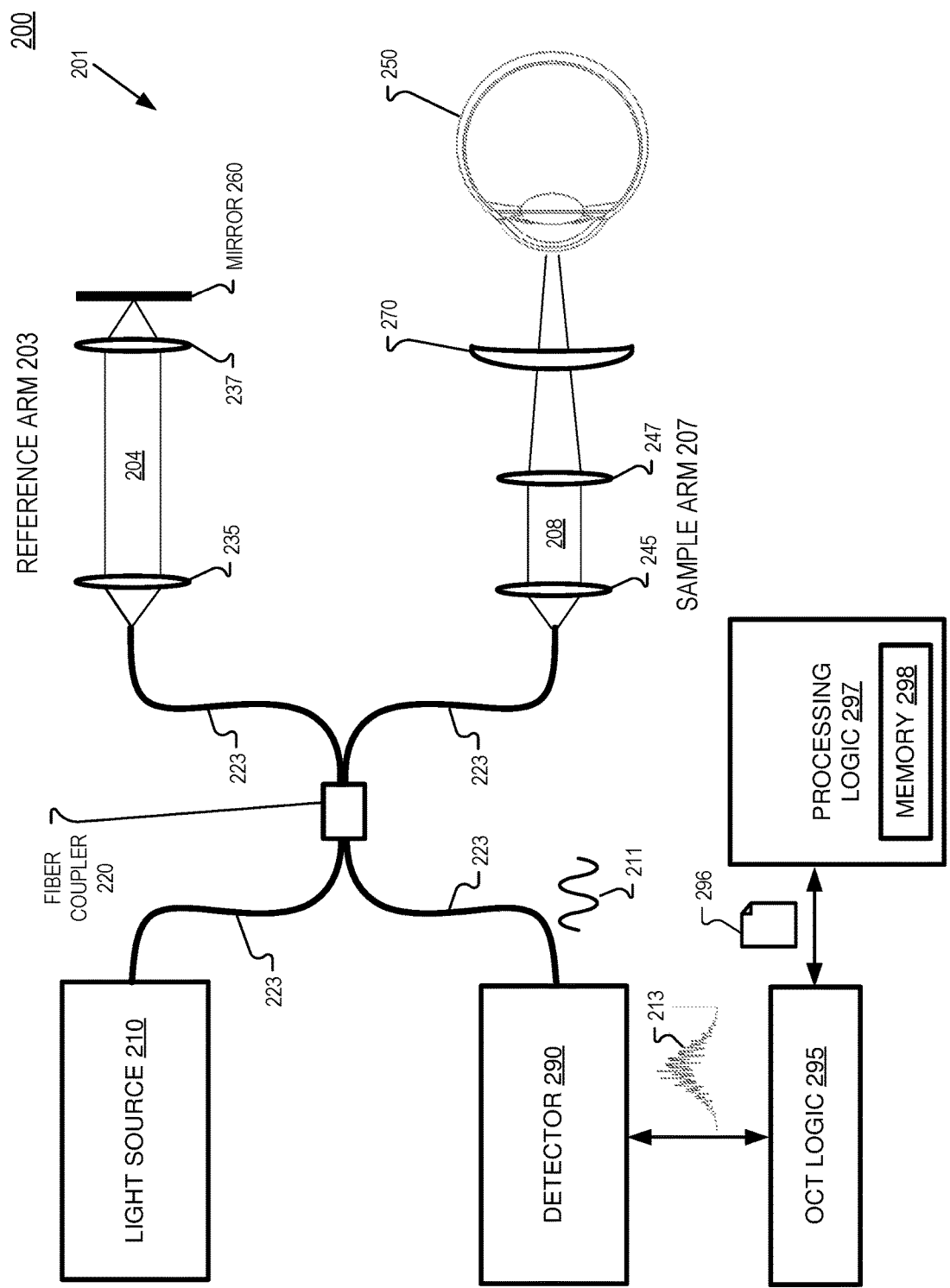
FIG. 2 illustrates an example system that includes an optical coherence tomography (OCT) device that may be utilized to capture volumetric ocular depth images that include prescription lenses and the eyes of a wearer of the prescription lenses, in accordance with aspects of the disclosure.

FIG. 2 illustrates an example system 200 that includes an optical coherence tomography (OCT) device 201 that may be utilized to capture volumetric ocular depth images that include prescription lenses and the eyes of a wearer of the prescription lenses, in accordance with aspects of the disclosure. The illustrated OCT system 200 is a Fourier-domain OCT system rather than a time-domain OCT system. In time-domain OCT systems, a reference mirror of the reference arm is moved axially during the signal acquisition whereas the reference mirror is kept stationary in Fourier-domain OCT systems. Fourier-domain OCT system 200 may be a spectral-domain OCT system or a swept-source OCT system. When system 200 is a spectral-domain OCT system, light source 210 includes a broadband light source and detector 290 includes a spectrometer. When system 200 is a swept-source OCT system, light source 210 includes a swept laser source and detector 290 includes a photodetector. OCT system 200 is one example of an imaging system that may capture volumetric ocular depth images that include prescription lenses and the eyes of the wearer of the prescription lenses.

System 200 includes OCT device 201 that includes a light source 210, a reference arm 203, a sample arm 207, a fiber coupler 220, a detector 290, and OCT logic 295. System 200 also includes processing logic 297 that includes memory 298. In some embodiments, memory 298 may be external to processing logic 297 and processing logic 297 is configured to read and/or write to the external memory.

OCT device 201 is configured to capture a volumetric ocular depth image 296 that includes imaging of prescription lens 270 and at least a portion of eye 250. In addition to the eye 250 of a wearer of prescription lens 270, the volumetric ocular depth image 296 may also include portions of an eye region of the face of a wearer of prescription lens 270 such that volumetric ocular depth image 296 captures a three-dimensional image of the prescription lens 270 with respect to the face and/or eye of the wearer of prescription lens 270.

Light source 210 may include a non-visible light source that illuminates optical fiber 223 with illumination light that encounters fiber coupler 220. Non-visible light may be defined as light having wavelengths that are outside the visible light range, such as ultraviolet light and infrared light. In aspects of this disclosure, visible light may be defined as having a wavelength range of approximately 380 nm-700 nm. Infrared light having a wavelength range of approximately 700 nm-1 mm includes near-infrared light. In aspects of this disclosure, near-infrared light may be defined as having a wavelength range of approximately 700 nm-1.4 µm. Using infrared light allows for shallow penetration into a sample such that a depth below skin or eyes may be imaged. Consequently, a volumetric ocular depth image 296 captured by system 200 may include a depth into the eye beyond the surface of the cornea. In an example spectral-domain OCT embodiment, light source 210 is a broadband light source emitting non-visible illumination light centered around 840 nm. In an example swept-source OCT embodiment, light source 210 is a swept-source laser. Fiber coupler 220 may be a 2×2 fiber coupler that splits the illumination light between the reference arm 203 and sample arm 207. Reference arm 203 may include optical elements 235 and 237 to focus the reference light 204 to reference mirror 260. Sample arm 207 may include optical elements 245 and 247 to focus the sample light 208 to the sample (the prescription lens 270 and eye 250, in the illustrated example). Reference mirror 260 may be positioned at an optical pathlength between prescription lens 270 and eye 250.

Backscattered light from the prescription lens 270 and eye 250 or face (not illustrated) interfere at fiber coupler 220 to generate optical interference signal 211 that is received by detector 290. Detector 290 generates an OCT signal 213 from the optical interference signal 211. Surfaces of the sample that backscatter a significant amount of light will cause interferences of greater intensity. In an example spectral-domain OCT embodiment, detector 290 is a 250 kHz spectrometer. In an example swept-source OCT embodiment, detector 290 is a photodiode.

Figure 4A:
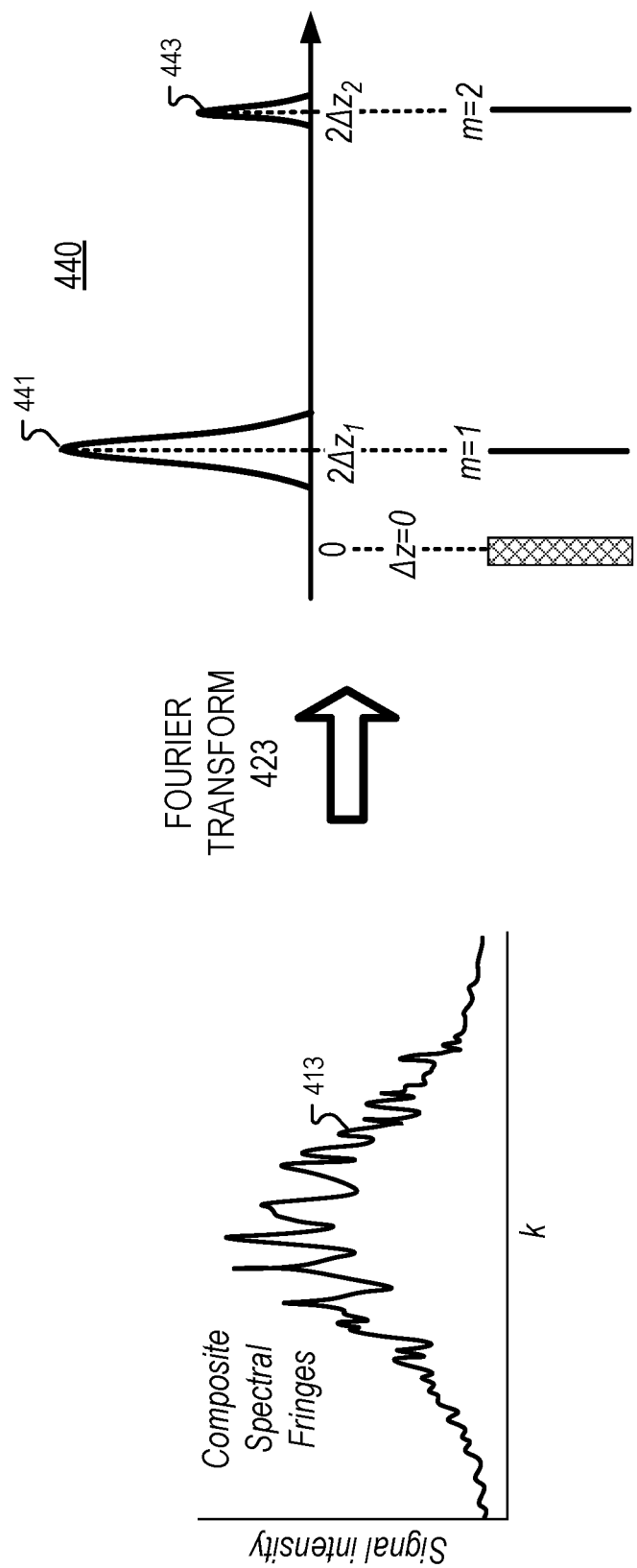
FIG. 4A illustrates that a Fourier Transform of an OCT signal generates a depth profile and that the peaks of the depth profile are representative of backscattering surfaces of the sample, in accordance with aspects of the disclosure.

FIG. 4A illustrates that a Fourier Transform 423 of an OCT signal 413 generates a depth profile 440 and that the peaks 441 and 443 of depth profile 440 are representative of backscattering surfaces of the sample. In FIG. 4A, peak 441 may be generated by a backscattering of a first surface of prescription lens 270 and peak 443 may be generated by a backscattering of a second surface of prescription lens 270, for example. Other surfaces of the sample such as the cornea, limbus, iris/pupil, and/or lens may also generate backscattered light that contributes to a depth profile. Thus, a depth profile may be generated from each OCT signal (e.g. 213) generated by an OCT device (e.g. OCT device 201).

Figure 5:
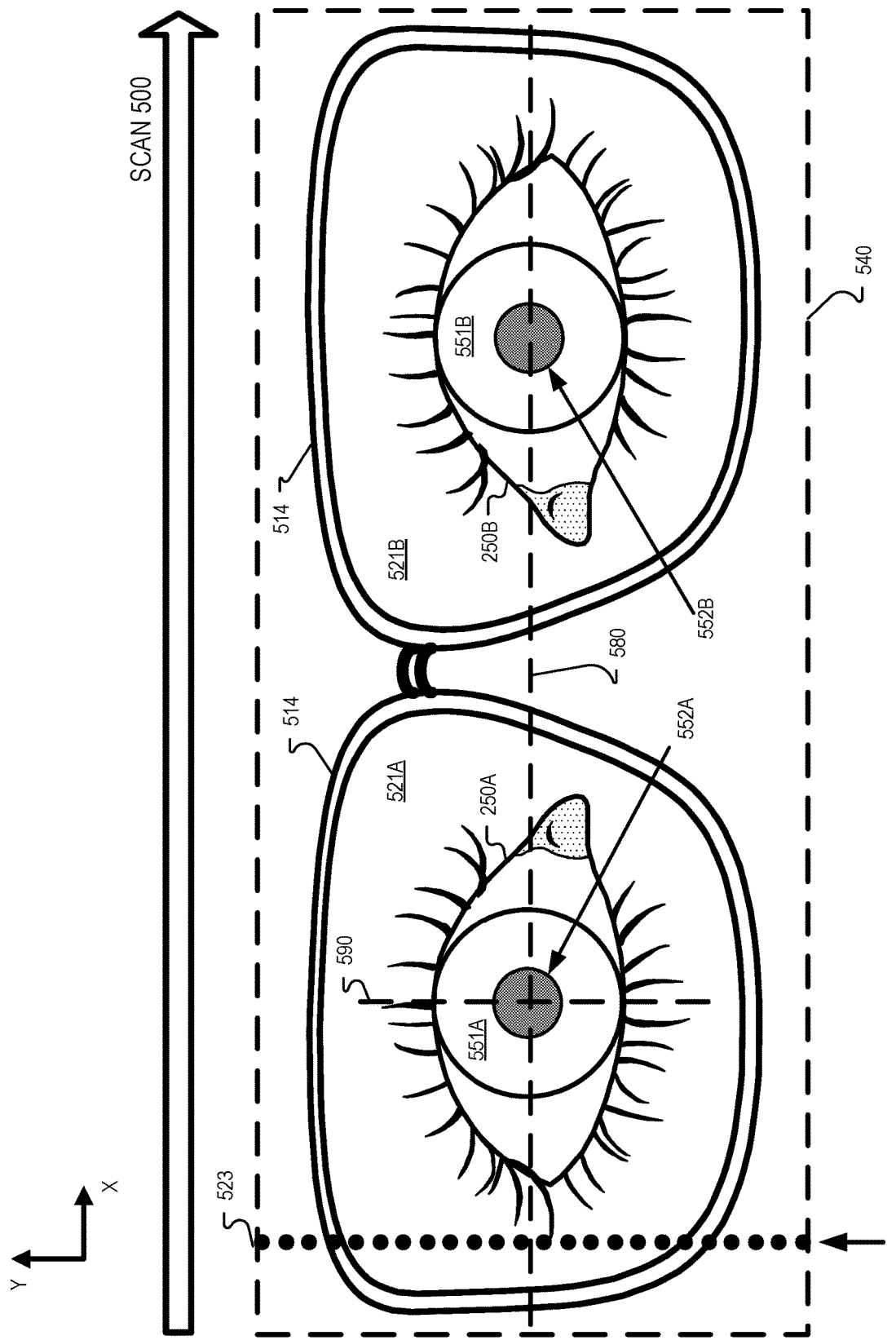
FIG. 5 illustrates an example scan of a person wearing eyeglasses including frames configured to hold prescription lenses in position on the face of a wearer of the prescription lenses, in accordance with aspects of the disclosure.

FIG. 5 illustrates an example scan 500 of a person wearing eyeglasses including frames 514 configured to hold prescription lenses 521A and 521B in position on the face of a wearer of the prescription lenses 521A and 521B. In a scan 500 to acquire a volumetric ocular depth image, a plurality of depth profiles 523 are acquired to generate a volumetric ocular depth image over example scan field 540. Example scan field 540 includes both prescription lenses 521A and 521B and eyes 250A and 250B, although the scan field in some embodiments may be more or less than scan field 540 in FIG. 5. Eyes 250 includes iris 551 and pupil 522, in FIG. 5. Capturing a volumetric ocular depth image may include scanning lines of depth profiles 523 across scan field 540. Example line 524 includes twenty-four depth profiles 523, for example. Some lines (e.g. line 524) may include 250 depth profiles 523 and 500 lines may be captured in a scan 500 going from left to right. Consequently, generating a volumetric ocular depth image (e.g. volumetric ocular depth image 296) may include capturing 125,000 depth profiles 523, in that example. Capturing each depth profile 523 may take approximately 4 μs. Other lateral positions and scan rates may also be utilized. OCT logic 295 may receive an OCT signal 213 for each depth profile 523, perform a Fourier Transform on each received OCT signal 213 to generate a depth profile for each OCT signal and then aggregate the depth profiles to generate a volumetric ocular depth image 296 of the entire scan field. In FIG. 2, the volumetric ocular depth image 296 is provided to processing logic 297 for further processing.

Figure 6A:
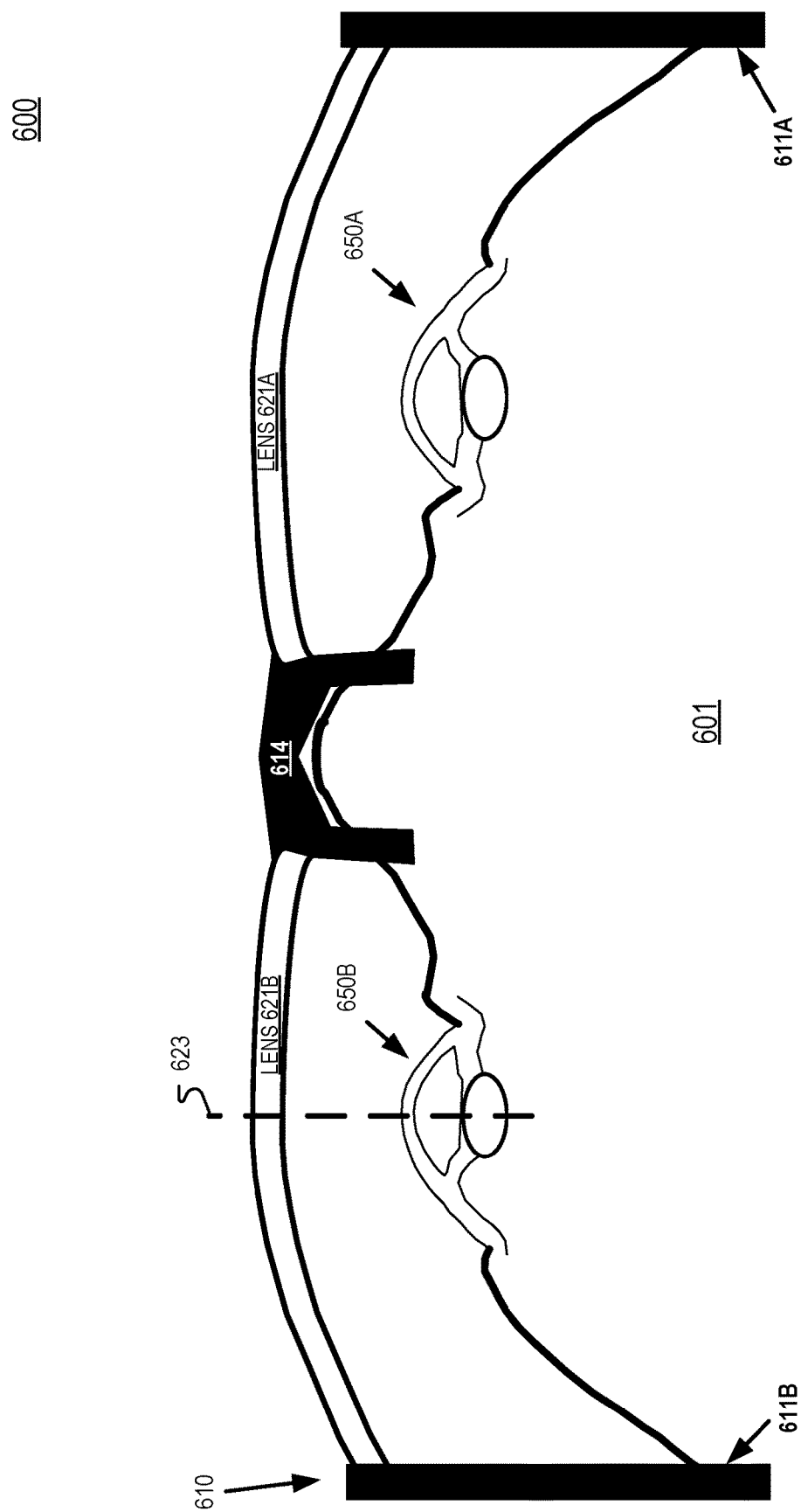
FIGS. 6A-6B illustrate a slice of a volumetric ocular depth image through a horizontal plane, in accordance with aspects of the disclosure.

FIG. 6A illustrates a slice 600 of a volumetric ocular depth image through a horizontal plane indicated by dashed-line 580 of FIG. 5, in accordance with aspects of the disclosure. Slice 600 may be generated by a plurality of depth profiles 623. Slice 600 shows that eyeglasses 610 include arms 611A and 611B attached to glasses frame 614 securing prescription lenses 621A and 621B. Prescription lens 621A corrects the vision of eye 650A of wearer 601 and prescription lens 621B corrects the vision of eye 650B of wearer 601.

Figure 6B:
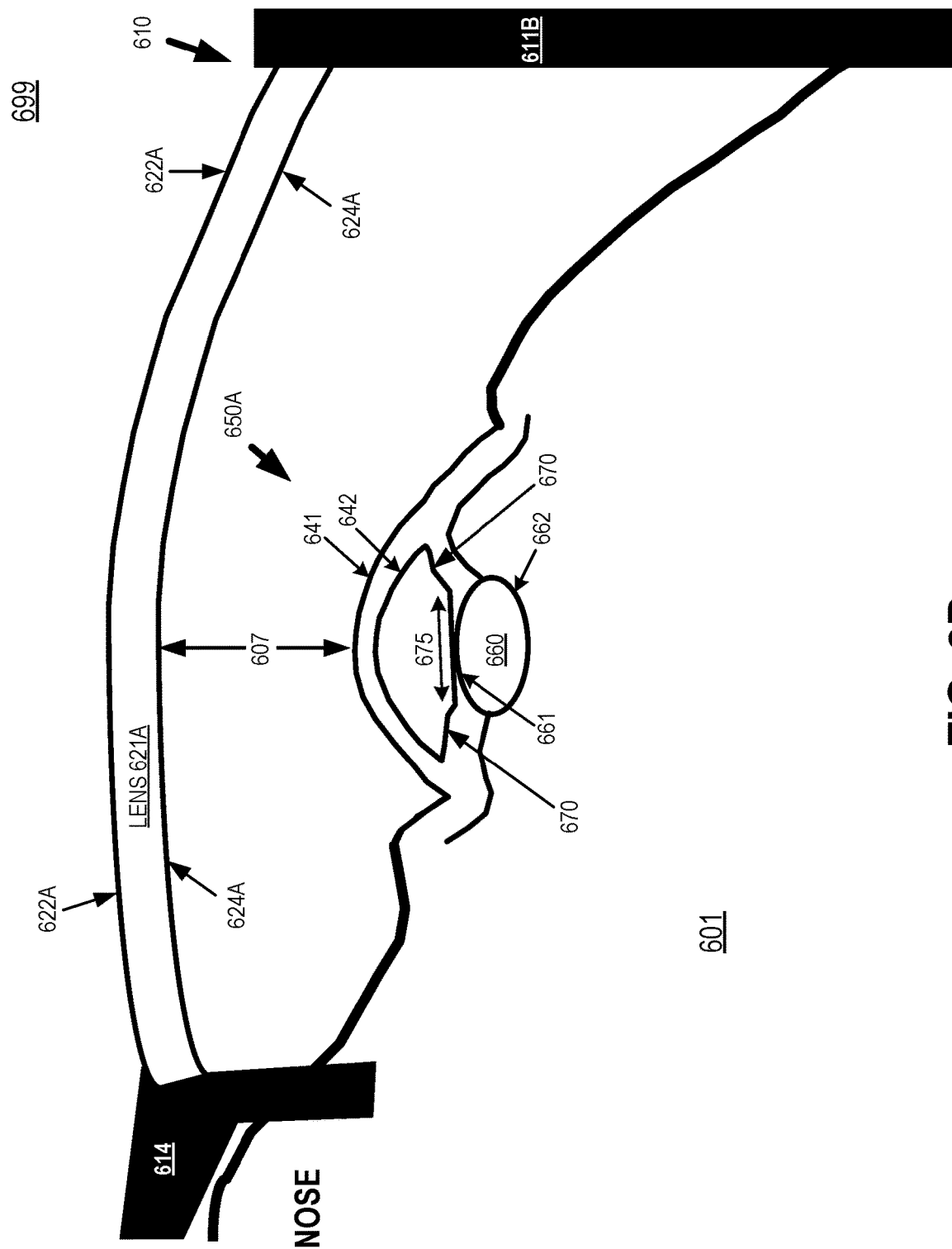

FIG. 6B illustrates a zoomed-in portion 699 of slice 600, in accordance with aspects of the disclosure. Prescription lens 621A of eyeglasses 610 includes a front surface 622A and a back surface 624A. An eye-relief measurement 607 may be determined from a front surface 641 of a cornea of eye 650A and a point on the back surface 624A of lens 621A. The front surface 641 of the cornea, the back surface 642 of the cornea, the front surface 661 of eye lens 660, the back surface 662 of eye lens 660, and iris 670 may also generate backscattered light that is significant enough to be imaged in a volumetric ocular depth image. Other features of eye 650A may also generate backscattered light that can be imaged by an OCT device such as OCT device 201. FIG. 6B illustrates that the skin around the eye and the nose of wearer 601 may also generate backscattered light that can be imaged by an OCT device. The pupil 675 of eye 650A may be determined by the space between iris 670. Although not shown in FIG. 6B, the retina of eye 650A may also be included in the volumetric ocular depth image.

Figure 7:
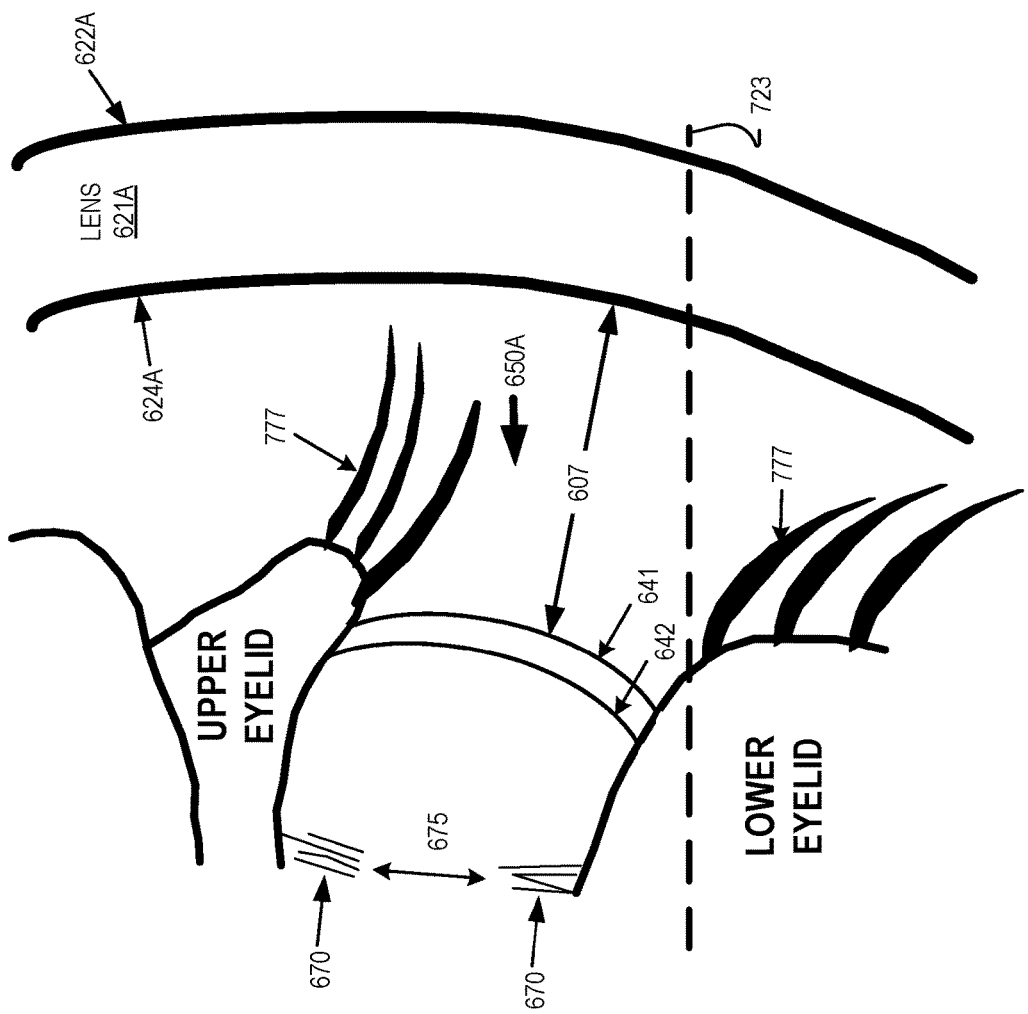
FIG. 7 illustrates a slice of a volumetric ocular depth image through a vertical plane, in accordance with aspects of the disclosure.

FIG. 7 illustrates a slice 700 of a volumetric ocular depth image through a vertical plane indicated by dashed-line 590 of FIG. 5, in accordance with aspects of the disclosure. Slice 700 may be generated by a plurality of depth profiles 723. Slice 700 includes an upper eyelid and a lower eyelid. The volumetric ocular depth image may even include eyelashes 777.

Slice 700 and slice 600 illustrate that a volumetric ocular depth image can include a full three-dimensional image of prescription lenses and the eyes and face of a wearer 601 of eyeglasses 610. Thus, lens-to-eye data that includes measurements of the prescription lens(es) with respect to the eye 650 can be generated. FIGS. 6B and 7 show eye-relief measurement 607 as one example of lens-to-eye data. In addition, a base curve of the front surface 622A and a back curve of back surface 624A of prescription lens 621A may also be generated since lens 621A is fully imaged in three-dimensions in the volumetric ocular depth image. For the purposes of the disclosure, the term "base curve" is associated with the profile of the front surface (e.g. 622A) of a prescription lens and the term "back curve" is associated with the profile of the back surface (e.g. 624A) of the prescription lens.

FIG. 8A illustrates that when both eyes 650A and 650B are included in a volumetric ocular depth image, an inter-pupillary distance (IPD) 817 can also be derived from the distance between a first pupil 675A of eye 650A and a second pupil 675B of eye 650B. A pupil size (e.g. diameter) of pupils 675 may also be measured from a volumetric ocular depth image.

FIG. 8B illustrates that an eye-relief measurement 807 from a volumetric ocular depth image can be measured from any point of the cornea of the eye to any point on the back surface of lens 821. FIG. 8C illustrates a frame tilt angle 809 from a volumetric ocular depth image can be measured to derive the angle at which glasses frames (not illustrated) hold the prescription lens(es) 821 with respect to a vertical plane.

Figure 3A:
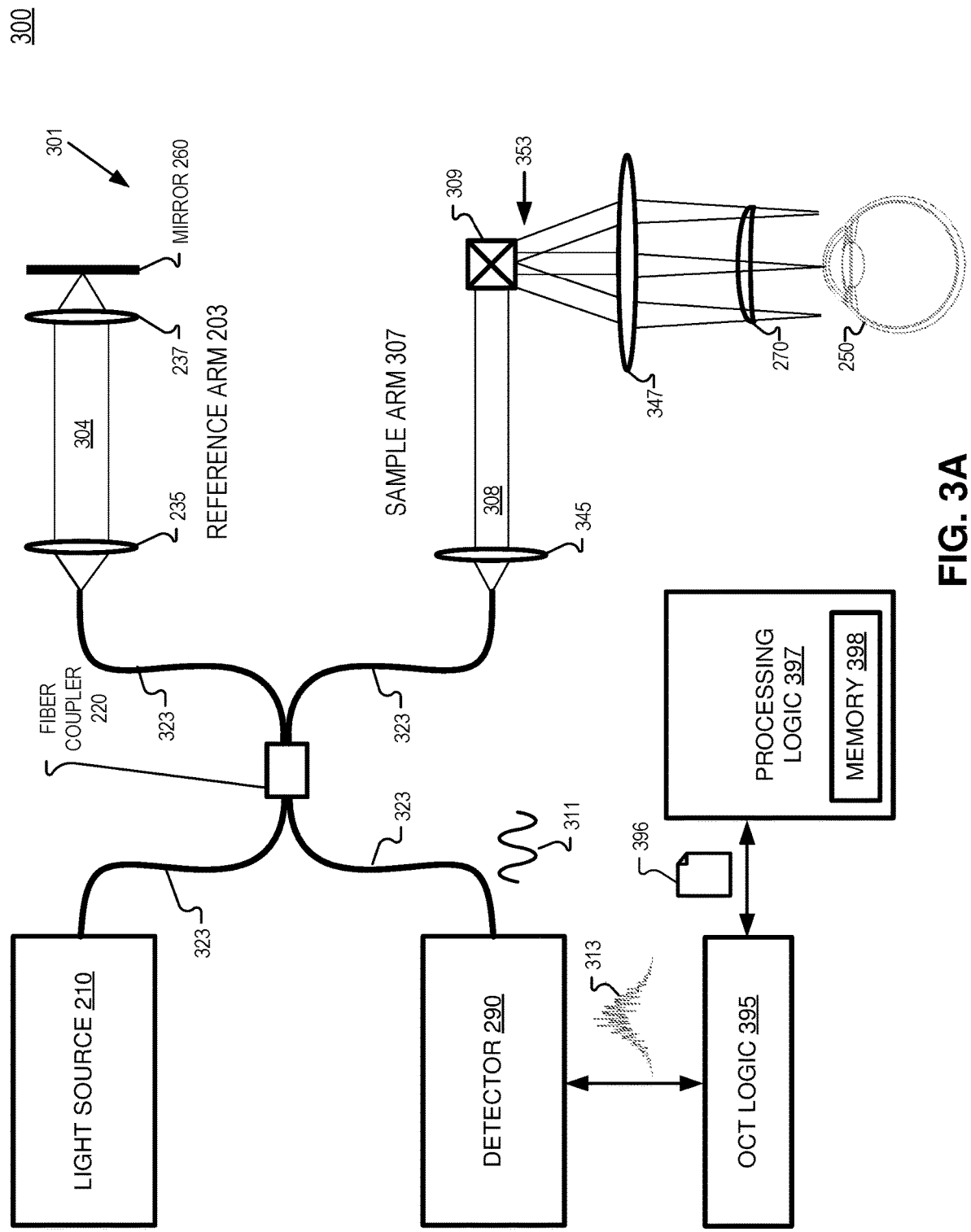
FIGS. 3A-3B illustrate another example system that includes an optical coherence tomography (OCT) device that includes a scanner that may be utilized to capture volumetric ocular depth images that include prescription lenses and the eyes of a wearer of the prescription lenses, in accordance with aspects of the disclosure.

FIG. 3A illustrates another example system 300 that includes an optical coherence tomography (OCT) device 301 that may be utilized to capture volumetric ocular depth images that include prescription lenses and the eyes of a wearer of the prescription lenses, in accordance with aspects of the disclosure. The illustrated OCT system 300 is a Fourier-domain OCT system similar to OCT system 200 where a two-dimensional scanner 309 and a scan or eyepiece lens 347 has been included in sample arm 307. Scanner 309 may be implemented with a micro-electro-mechanical systems (MEMS) micro-mirror to quickly direct light 308 to different regions of a scan field (e.g. scan field 540) of eye 250.

Figure 3B:
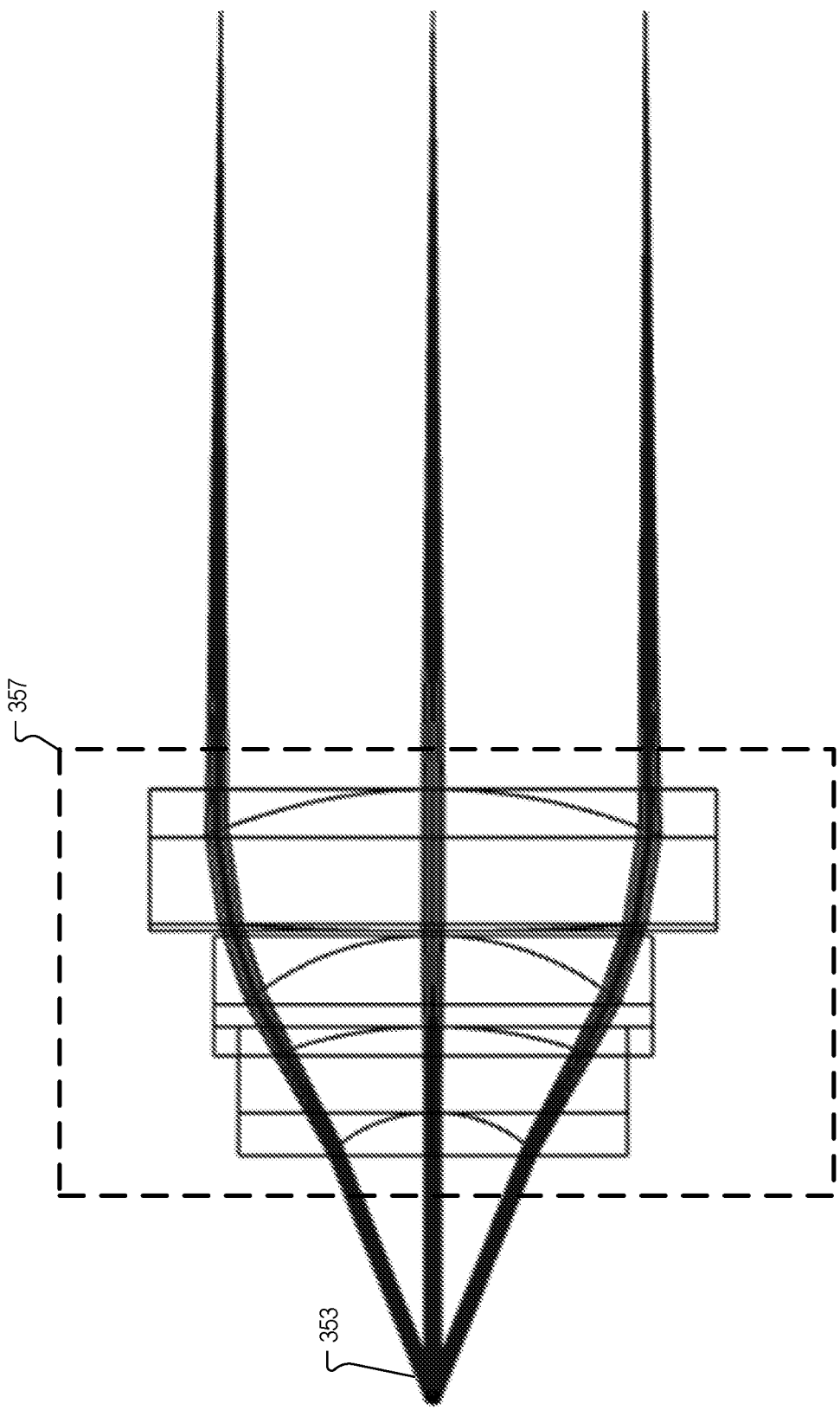

FIG. 3B illustrates an example scan lens 357 configured to distribute light 308 from an exit point 353 of scanner 309 to a particular focus point for a particular depth profile. In other words, scanner 309 may direct light 308 at a variety of angles when capturing different depth profiles 523 to cover the scan field and scan lens 357 is configured to direct the light 308 to the sample and focus backscattered light from the sample back to scanner 309 to be reflected back to fiber coupler 220 via the optical fiber 323.

OCT device 301 is configured to capture a volumetric ocular depth image 396 that includes prescription lens 270 and at least a portion of eye 250. In addition to the eye 250 of a wearer of prescription lens 270, the volumetric ocular depth image 396 may also include portions of the face of a wearer of prescription lens 270 such that volumetric ocular depth image 396 captures a three-dimensional image of the prescription lens 270 with respect to the face and/or eye 250 of the wearer of prescription lens 270. System 300 also includes processing logic 397 that includes memory 398. In some embodiments, memory 398 may be external to processing logic 397 and processing logic 397 is configured to read and/or write to the external memory. As in system 200, reference mirror 260 of system 300 may be positioned at an optical pathlength between prescription lens 270 and eye 250.

Backscattered light from the prescription lens 270 and eye 250 or face (not illustrated) interfere at fiber coupler 220 to generate optical interference signal 311 that is received by detector 290. Detector 290 generates an OCT signal 313 from the optical interference signal 311. A plurality of OCT signals 313 for a plurality of depth profiles may be aggregated to generate volumetric ocular depth image 396, in FIG. 3A.

Volumetric ocular depth images (e.g. images 296 or 396) provide a dense 3D image of the eye and/or face of a wearer with respect to prescription lenses. This allows for a reconstruction of the prescription surface profile of the prescription lens such that the optical power of the prescription lens, the base curve, and the back curve of the prescription lens can be known.

Figure 4B:
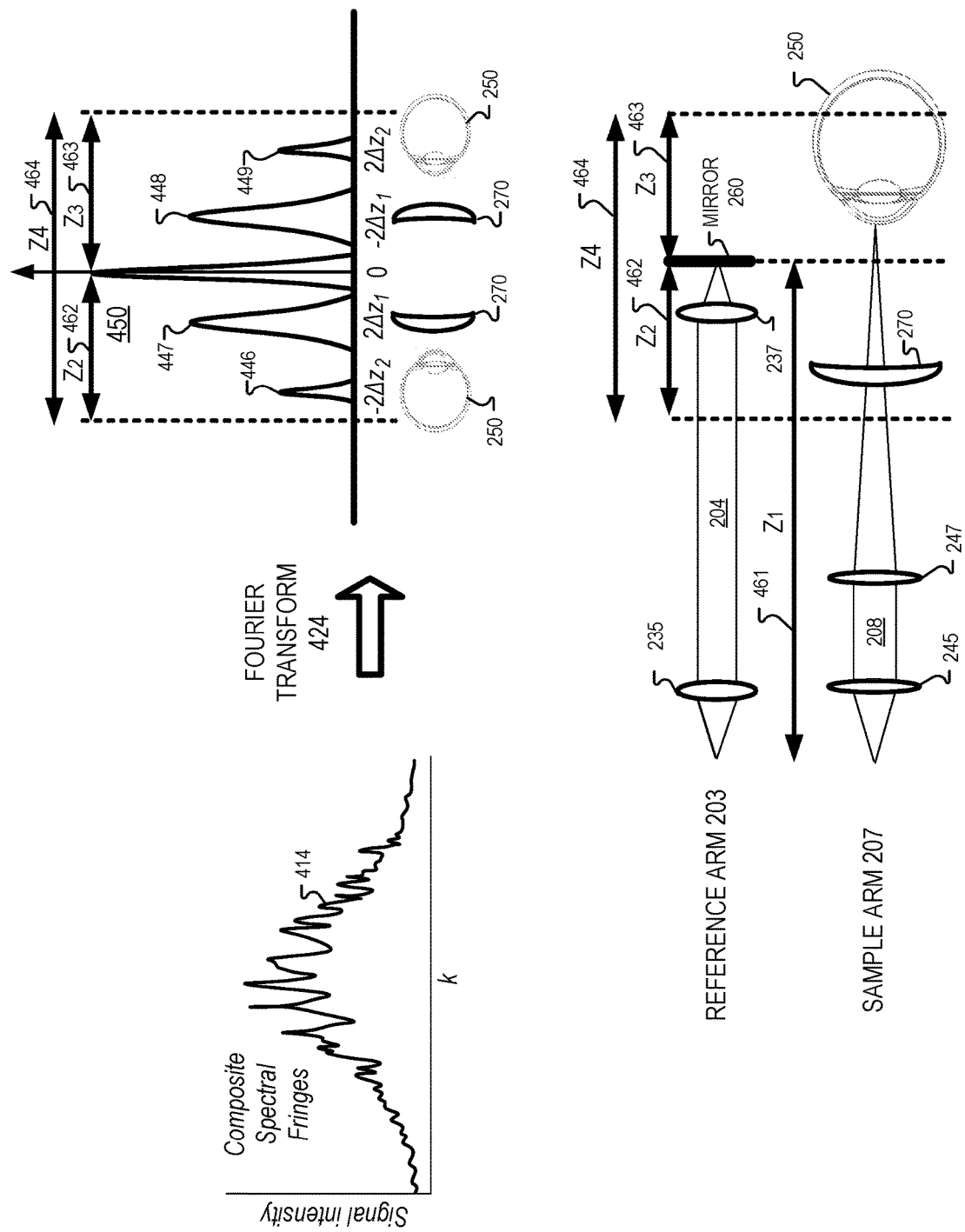
FIG. 4B illustrates an example depth profile generated from an OCT signal of an OCT system while a mirror of a reference arm of the OCT system is positioned at an optical pathlength between an eye of a user and a prescription lens worn by the user, in accordance with aspects of the disclosure.

FIG. 4B illustrates an example depth profile 450 generated from an OCT signal of an OCT system while a mirror of a reference arm of the OCT system is positioned at an optical pathlength between an eye of a user and a prescription lens worn by the user, in accordance with aspects of the disclosure. An OCT system such as OCT system 200 or 300 generates an OCT signal 414 while mirror 260 of reference arm 203 is positioned at an optical pathlength Z1 461 between an eye 250 of a user and a prescription lens 270 worn by the user.

A Fourier Transform 424 of OCT signal 414 generates a depth profile 450 and peaks 446, 447, 448, and 449 of depth profile 450 are representative of backscattering surfaces of the sample. In FIG. 4B, peak 447 may be generated by a backscattering of prescription lens 270 and peak 449 may be generated by a backscattering of eye 250, for example. In this example, peak 446 is a mirror image of peak 449 and peak 448 is a mirror image of peak 447 as a byproduct of performing a Fourier Transform on a "real" signal (as opposed to a signal that includes imaginary components). Thus, an imaging depth Z4 464 may include both a first imaging depth Z2 462 that is beyond the optical pathlength Z1 461 of mirror 260 and a second imaging depth Z3 463 that is before the optical pathlength Z1 461 of mirror 260. Peaks associated with mirror images may need to be filtered out of depth profile 450 so duplicate surfaces are not imaged. In the example of FIG. 4B, peak 448 and peak 446 may be filtered out of depth profile since they are duplicate (mirror images) of peak 447 and peak 449, respectively.

Surfaces of eye 250 that generate peaks included in depth profile 450 may include a cornea, a limbus, an iris/pupil, and/or lens. A depth profile may be generated from each OCT signal (e.g. 213) generated by an OCT system.

In an implementation, imaging depth Z4 464 is greater than 16 mm. In an implementation, imaging depth Z4 464 is greater than 20 mm. In an implementation, imaging depth Z4 464 is approximately 24 mm. First imaging depth Z2 462 may be equal to second imaging depth Z3 463.

Figure 9:
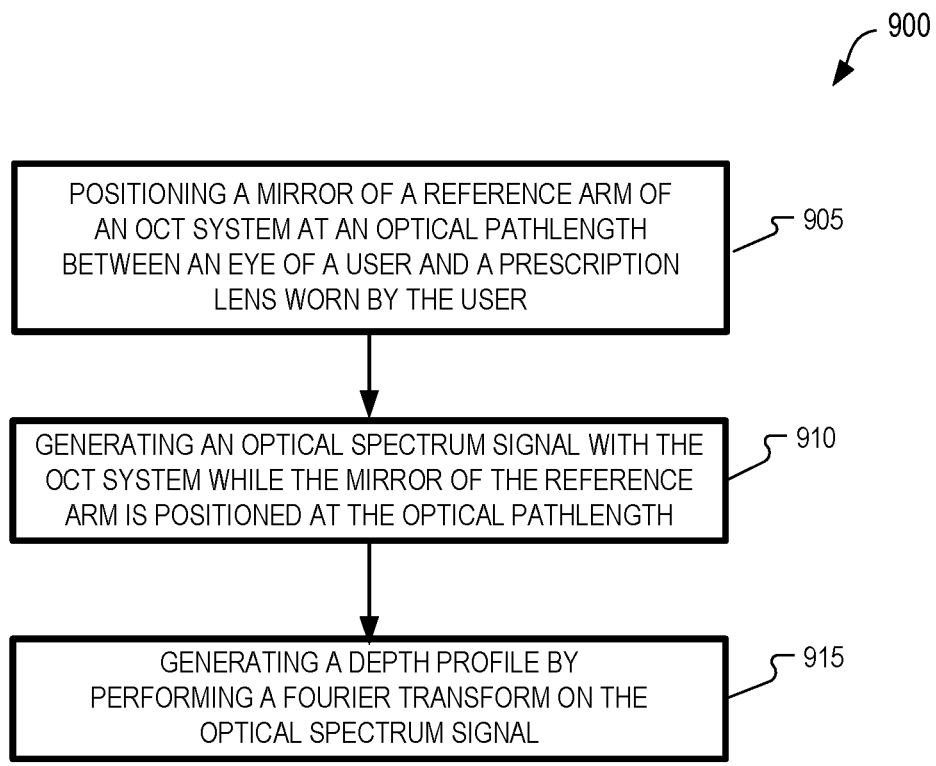
FIG. 9 illustrates a flow chart of an example process of generating a depth profile, in accordance with aspects of the disclosure.

FIG. 9 illustrates a flow chart of an example process of generating a depth profile, in accordance with aspects of the disclosure. The order in which some or all of the process blocks appear in process 900 should not be deemed limiting. Rather, one of ordinary skill in the art having the benefit of the present disclosure will understand that some of the process blocks may be executed in a variety of orders not illustrated, or even in parallel.

In process block 905, a mirror of a reference arm of an OCT system is positioned at an optical pathlength between an eye of a user and a prescription lens worn by the user.

An OCT signal (e.g. OCT signal 213 or 414) is generated with the OCT system while the mirror of the reference arm is positioned at the optical pathlength that is between the eye and the prescription lens, in process block 910. In one implementation, the OCT signal is generated by reflections from at least a front surface of the prescription lens, a back surface of the prescription lens, and a cornea of the eye.

In process block 915, a depth profile is generated by performing a Fourier Transform on the OCT signal. The depth profile includes the prescription lens and at least a portion of the eye of the user. In an implementation of process 900, an imaging depth of the depth profile is greater than 16 mm. The imaging depth of the depth profile may be greater than 20 mm. In an implementation, the imaging depth is approximately 24 mm.

Process 900 may further include generating a volumetric ocular depth image based on aggregating the depth profile and a plurality of subsequent depth profiles captured by the OCT system while the mirror of the reference arm is positioned at the optical pathlength, wherein the volumetric ocular depth image includes the eye of the user and the prescription lens worn by the user. In this implementation, subsequent depth profiles are captured by the OCT system at different positions, as shown in FIG. 5 of the disclosure. For example, lines 524 of depth profiles 523 may be generated to generate the volumetric ocular depth image slice-by-slice while the mirror of the reference arm is positioned at an optical path between the prescription lens and the eye. The volumetric ocular depth image may include at least one of an eye-relief distance with respect to the prescription lens, a lens-to-cornea distance, an interpupillary distance of the eye with respect to a second eye of the user, a pupil size of the eye, or a corneal topography of the eye, in some implementations. The eye-relief distance may be defined as from a back surface of the prescription lens to a cornea of the eye. The volumetric ocular depth image may include a base curve of a front surface of the prescription lens and a back curve of a back surface of the prescription lens.

In an implementation of process 900, the optical pathlength to position the mirror of the reference arm is determined prior to positioning the mirror of the reference arm to the optical pathlength. Of course, in this implementation, positioning the mirror to the optical pathlength is performed subsequent to determining the optical pathlength.

Figure 10:
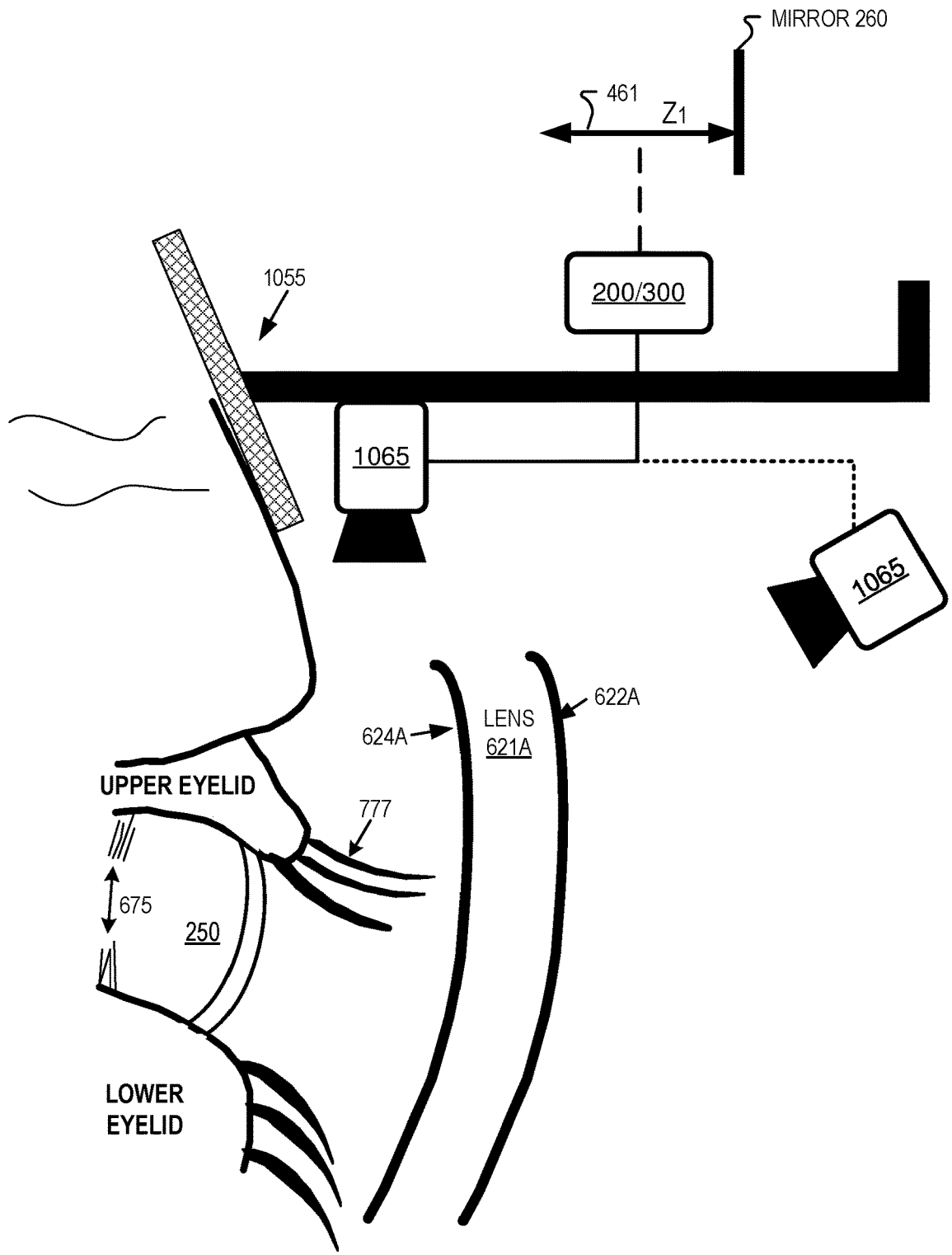
FIG. 10 illustrates an example OCT system for determining the optical pathlength for adjusting the mirror of the reference arm to, in accordance with an embodiment of the disclosure.

FIG. 10 illustrates an example OCT system 1000 for determining the optical pathlength for adjusting the mirror of the reference arm to, in accordance with aspects of the disclosure. OCT system 1000 includes a sensor 1065 for capturing sensor data that includes a lens-position relative to a reference point of OCT system 1000. FIG. 10 illustrates that sensor 1065 may be positioned in a variety of locations. Sensor 1065 is configured to provide sensor data to OCT system 200/300 that is included in OCT system 1000. OCT system 1000 includes facial support apparatus 1055 to assist in keeping the head/eye of a user relatively still while generating depth profiles. Facial support apparatus 1055 engages a forehead of the user in the illustrated embodiment, but facial support apparatus 1055 may also engage a chin or cheek-area of the user, in some embodiments. Sensor 1065 may be positioned in a fixed location with respect to facial support apparatus 1055 such that sensor 1065 is positioned at a known reference point of a sample arm of OCT system 1000. Sensor 1065 may be implemented as structured light depth sensors, stereo cameras, time-of-flight (TOF) cameras, low f-number camera or no f-number camera with a shallow depth of field, LIDAR, or otherwise. Where sensor 1065 is a camera, the camera may capture an image that includes lens 621A and eye 202. An optical pathlength Z1 461 of mirror 260 may be adjusted based on the position of lens 621A and eye 250 in the image so that the mirror is positioned between lens 621A and eye 250 so that a depth profile generated by OCT system 1000 includes the prescription lens 621A and at least a portion of eye 250.

In some implementations of process 900, determining the optical pathlength for the mirror of the reference arm includes capturing sensor data with a sensor (e.g. sensor 1065). The sensor data includes a lens-position of the prescription lens relative to a reference point of the OCT system. Positioning the mirror of the reference arm to the optical pathlength between the eye of the user and the prescription lens is based at least in part on the sensor data, in these implementations.

In an implementation of process 900, determining the optical pathlength includes identifying a first peak and a second peak of preliminary Fourier Transform data generated from a preliminary OCT signal generated by the OCT system where the first peak is associated with the prescription lens and the second peak is associated with the eye of the user. For example, the optical pathlength Z1 461 of mirror 260 may be adjusted until a preliminary depth profile from a preliminary Fourier Transform includes a first peak (e.g. 447) associated with the prescription lens and a second peak (e.g. 449) associated with the eye. Once the first peak and second peak are included in the preliminary depth profile (indicating the mirror 260 was at an optical pathlength between the eye and the prescription lens), a scan (e.g. scan 500) may commence to capture a plurality of depth profiles.

Figure 11:
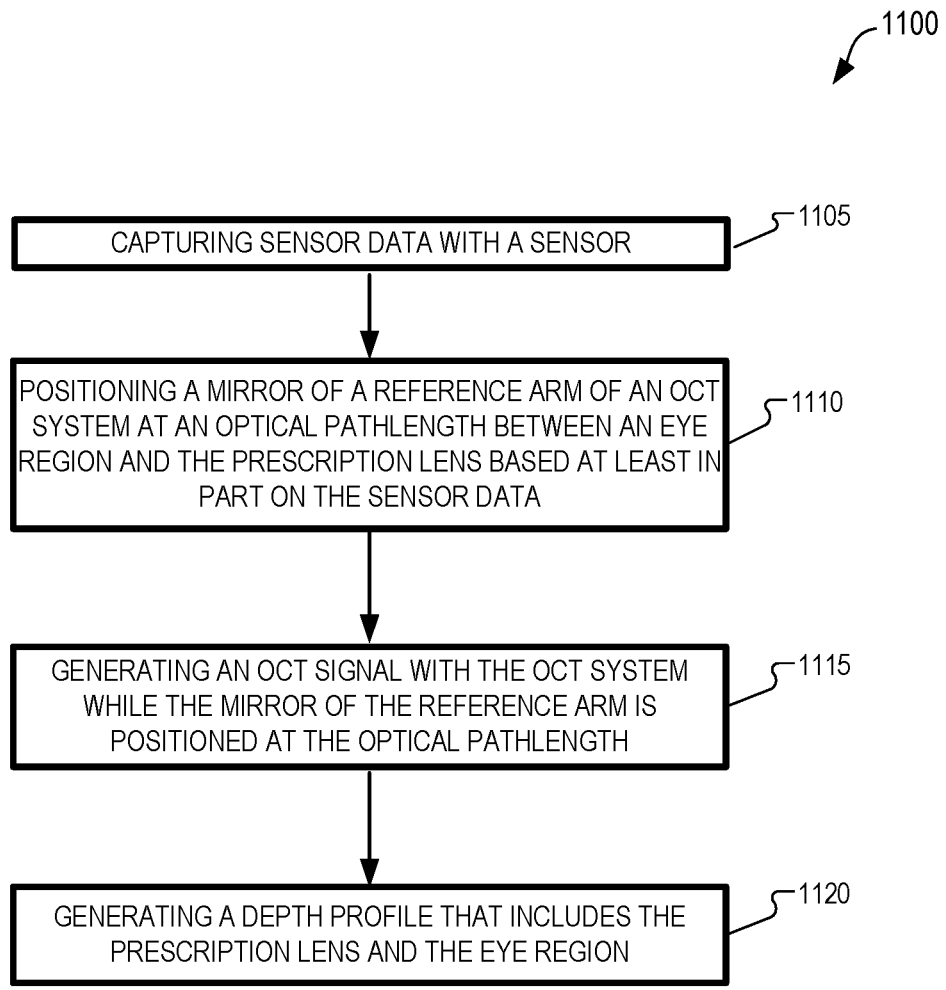
FIG. 11 illustrates a flow chart of an example process of generating a depth profile, in accordance with aspects of the disclosure.

FIG. 11 illustrates a flow chart of an example process of generating a depth profile, in accordance with aspects of the disclosure. The order in which some or all of the process blocks appear in process 900 should not be deemed limiting. Rather, one of ordinary skill in the art having the benefit of the present disclosure will understand that some of the process blocks may be executed in a variety of orders not illustrated, or even in parallel.

In process block 1105, sensor data is captured by a sensor (e.g. sensor 1065). The sensor data includes a lens-position of a prescription lens relative to a reference point of an OCT system (e.g. OCT system 1000). The sensor may include at least one of an image sensor, a structured light depth sensors, stereo cameras, time-of-flight (TOF) cameras, low f-number camera or no f-number camera with a shallow depth of field, or a LIDAR system.

In process block 1110, a mirror of a reference arm of the OCT system is positioned at an optical pathlength between an eye region and the prescription lens based at least in part on the sensor data.

In process block 1115, an OCT signal is generated with the OCT system while the mirror of the reference arm is positioned at the optical pathlength.

In process block 1120, a depth profile that includes the prescription lens and the eye region is generated.

Process 1100 may further include capturing a preliminary OCT signal with the OCT system. The positioning of the mirror of the reference arm at the optical pathlength is also based on the preliminary OCT signal. The preliminary OCT signal may be captured subsequent to capturing the sensor data. In some implementations, process 1100 may further include identifying a first peak of preliminary Fourier Transform data generated from the preliminary OCT signal and identifying a second peak of the preliminary Fourier Transform data. The first peak is associated with the prescription lens and the second peak is associated with the eye of the user.

In an implementation of process 1100, a volumetric ocular depth image may be generated based on aggregating the depth profile and a plurality of subsequent depth profiles captured by the OCT system while the mirror of the reference arm is position at the optical pathlength. The volumetric depth image includes an eye of the user and the prescription lens worn by a user. The volumetric ocular depth image may include at least one of (1) an eye-relief distance with respect to the prescription lens; (2) a lens-to-cornea distance; (3) an interpupillary distance of the eye with respect to a second eye of the user; (4) a pupil size of the eye; or (5) a corneal topography of the eye. The eye-relief distance is from a back surface of the prescription lens to a cornea of the eye. The volumetric ocular depth image may include a base curve of a front surface of the prescription lens and a base curve of a back surface of the prescription lens.

Embodiments of the invention may include or be implemented in conjunction with an artificial reality system. Artificial reality is a form of reality that has been adjusted in some manner before presentation to a user, which may include, e.g., a virtual reality (VR), an augmented reality (AR), a mixed reality (MR), a hybrid reality, or some combination and/or derivatives thereof. Artificial reality content may include completely generated content or generated content combined with captured (e.g., real-world) content. The artificial reality content may include video, audio, haptic feedback, or some combination thereof, and any of which may be presented in a single channel or in multiple channels (such as stereo video that produces a three-dimensional effect to the viewer). Additionally, in some embodiments, artificial reality may also be associated with applications, products, accessories, services, or some combination thereof, that are used to, e.g., create content in an artificial reality and/or are otherwise used in (e.g., perform activities in) an artificial reality. The artificial reality system that provides the artificial reality content may be implemented on various platforms, including a head-mounted display (HMD) connected to a host computer system, a standalone HMD, a mobile device or computing system, or any other hardware platform capable of providing artificial reality content to one or more viewers.

The term "logic" or "processing logic" in this disclosure may include one or more processors, microprocessors, multi-core processors, Application-specific integrated circuits (ASIC), and/or Field Programmable Gate Arrays (FPGAs) to execute operations disclosed herein. In some embodiments, memories (not illustrated) are integrated into the processing logic to store instructions to execute operations and/or store data. Processing logic may also include analog or digital circuitry to perform the operations in accordance with embodiments of the disclosure.

A "memory" or "memories" described in this disclosure may include one or more volatile or non-volatile memory architectures. The "memory" or "memories" may be removable and non-removable media implemented in any method or technology for storage of information such as computer-readable instructions, data structures, program modules, or other data. Example memory technologies may include RAM, ROM, EEPROM, flash memory, CD-ROM, digital versatile disks (DVD), high-definition multimedia/data storage disks, or other optical storage, magnetic cassettes, magnetic tape, magnetic disk storage or other magnetic storage devices, or any other non-transmission medium that can be used to store information for access by a computing device.

A computing device may include a desktop computer, a laptop computer, a tablet, a phablet, a smartphone, a feature phone, a server computer, or otherwise. A server computer may be located remotely in a data center or be stored locally.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible non-transitory machine-readable storage medium includes any mechanism that provides (i.e., stores) information in a form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A method, comprising:
    capturing sensor data with a sensor, wherein the sensor data includes a lens-position of a prescription lens relative to a reference point of an optical coherence tomography (OCT) system;
    positioning a mirror of a reference arm of the OCT system at an optical pathlength between an eye region and the prescription lens based at least in part on the sensor data;
    generating an OCT signal with the OCT system while the mirror of the reference arm is positioned at the optical pathlength;
    generating a depth profile that includes at least a first peak associated with the prescription lens, at least a second peak associated with the eye region, and duplicates of the at least the first peak and the at least the second peak; and
    filtering the duplicates out of the depth profile.

2. The method of claim 1, further comprising:
    capturing a preliminary OCT signal with the OCT system, wherein the positioning the mirror of the reference arm at the optical pathlength is also based on the preliminary OCT signal.

3. The method of claim 2, further comprising:
    identifying the at least the first peak in preliminary Fourier Transform data generated from the preliminary OCT signal generated by the OCT system; and
    identifying the at least the second peak in the preliminary Fourier Transform data.

4. The method of claim 2, wherein the preliminary OCT signal is captured subsequent to capturing the sensor data.

5. The method of claim 1, wherein the sensor includes at least one of an image sensor, a structured light depth sensors, stereo cameras, time-of-flight (TOF) cameras, low f-number camera with a shallow depth of field, or a light detection and ranging (LIDAR) system.

6. The method of claim 1, further comprising:
    generating a volumetric ocular depth image based on aggregating the depth profile and a plurality of subsequent depth profiles captured by the OCT system while the mirror of the reference arm is positioned at the optical pathlength, wherein the volumetric ocular depth image includes a first eye of a user and the prescription lens worn by the user.

7. The method of claim 6, wherein the volumetric ocular depth image includes at least one of: (1) an eye-relief distance with respect to the prescription lens; (2) a lens-to-cornea distance; (3) an interpupillary distance of the first eye with respect to a second eye of the user; (4) a pupil size of the first eye; or (5) a corneal topography of the first eye, and wherein the eye-relief distance is from a back surface of the prescription lens to a cornea of the first eye.

8. The method of claim 6, wherein the volumetric ocular depth image includes a base curve of a front surface of the prescription lens and a back curve of a back surface of the prescription lens.

9. The method of claim 1, wherein the OCT system is a Fourier-domain OCT system including a light source to illuminate the eye region, the prescription lens, and the mirror of the reference arm.

10. A non-transitory machine-accessible storage medium that provides instructions that, when executed by processing logic, will cause the processing logic to perform operations comprising:
    capturing sensor data with a sensor, wherein the sensor data includes a lens-position of a prescription lens relative to a reference point of an optical coherence tomography (OCT) system;
    positioning a mirror of a reference arm of the OCT system at an optical pathlength between an eye region and the prescription lens based at least in part on the sensor data;
    generating an OCT signal with the OCT system while the mirror of the reference arm is positioned at the optical pathlength;
    generating a depth profile that includes the prescription lens and the eye region; and
    filtering duplicate peaks, associated with the prescription lens and the eye region, out of the depth profile.

11. The non-transitory machine-accessible storage medium of claim 10, wherein the non-transitory machine-accessible storage medium provides further instructions that will cause the processing logic to perform further operations comprising:

capturing a preliminary OCT signal with the OCT system, wherein the positioning the mirror of the reference arm at the optical pathlength is also based on the preliminary OCT signal.

12. The non-transitory machine-accessible storage medium of claim 11, wherein the non-transitory machine-accessible storage medium provides further instructions that will cause the processing logic to perform further operations comprising:

identifying a first peak of preliminary Fourier Transform data generated from the preliminary OCT signal generated by the OCT system, wherein the first peak is associated with the prescription lens; and identifying a second peak of the preliminary Fourier Transform data, wherein the second peak is associated with an eye of a user.

13. The non-transitory machine-accessible storage medium of claim 11, wherein the preliminary OCT signal is captured subsequent to capturing the sensor data.

14. The non-transitory machine-accessible storage medium of claim 10, wherein the sensor includes at least one of an image sensor, a structured light depth sensors, stereo cameras, time-of-flight (TOF) cameras, low f-number camera or no f-number camera with a shallow depth of field, or a light detection and ranging (LIDAR) system.

15. The non-transitory machine-accessible storage medium of claim 10, the non-transitory machine-accessible storage medium providing further instruction that will cause the processing logic to perform further operations comprising:

generating a volumetric ocular depth image based on aggregating the depth profile and a plurality of subsequent depth profiles captured by the OCT system while the mirror of the reference arm is positioned at the optical pathlength, wherein the volumetric ocular depth image includes a first eye of a user and the prescription lens worn by the user.

16. A system, comprising:

an optical coherence tomography (OCT) device configured to capture volumetric ocular depth images that includes a front surface of a prescription lens, a back surface of the prescription lens, and an eye region;

a sensor configured to generate sensor data that includes a lens-position of the prescription lens relative to a reference point of the OCT device;

a memory configured to store instructions; and processing logic configured to receive the volumetric ocular depth images from the OCT device, wherein the processing logic is also configured to access the instructions that when executed by the processing logic, cause the processing logic to perform operations comprising:

capturing sensor data with the sensor;

positioning a mirror of a reference arm of the OCT device at an optical pathlength between the eye region and the prescription lens based at least in part on the sensor data; and generating OCT signals with the OCT system while the mirror of the reference arm is positioned at the optical pathlength; and generating a volumetric ocular depth image based on the OCT signals, wherein duplicate surfaces are absent from the volumetric ocular depth image by filtering out duplicate peaks that represent interference intensity associated with the prescription lens and the eye region.

17. The system of claim 16, wherein the processing logic is configured to perform further operations comprising:

capturing a preliminary OCT signal with the OCT device, wherein the positioning the mirror of the reference arm at the optical pathlength is also based on the preliminary OCT signal.

18. The system of claim 17, wherein the processing logic is configured to perform further operations comprising:

identifying a first peak of preliminary Fourier Transform data generated from the preliminary OCT signal generated by the OCT device, wherein the first peak is associated with the prescription lens; and identifying a second peak of the preliminary Fourier Transform data, wherein the second peak is associated with an eye of a user.

19. The system of claim 16, further comprising:

a facial support to receive a head of a user of the OCT device.

20. The system of claim 16, wherein the OCT device is a Fourier-domain OCT system including a light source to illuminate the eye region, the prescription lens, and the mirror of the reference arm.

* * * * *